United States Patent
Li et al.

(10) Patent No.: US 12,168,807 B2
(45) Date of Patent: Dec. 17, 2024

(54) MULTIPLEXED NUCLEIC ACID DETECTION KIT FOR HUMAN PAPILLOMA VIRUS (HPV) TYPING, AND DETECTION METHOD

(71) Applicant: INNOVATION ACADEMY FOR PRECISION MEASUREMENT SCIENCE AND TECHNOLOGY, CHINESE ACADEMY OF SCIENCES, Wuhan (CN)

(72) Inventors: Ying Li, Wuhan (CN); Zhichen Xu, Wuhan (CN); Yunhuang Yang, Wuhan (CN); Tao Li, Wuhan (CN)

(73) Assignee: INNOVATION ACADEMY FOR PRECISION MEASUREMENT SCIENCE AND TECHNOLOGY, CHINESE ACADEMY OF SCIENCES, Wuhan (CN)

(*) Notice: Subject to any disclaimer, the term of this patent is extended or adjusted under 35 U.S.C. 154(b) by 0 days.

(21) Appl. No.: 18/512,036

(22) Filed: Nov. 17, 2023

(65) Prior Publication Data
US 2024/0150856 A1 May 9, 2024

Related U.S. Application Data

(63) Continuation of application No. PCT/CN2022/114122, filed on Aug. 23, 2022.

(30) Foreign Application Priority Data

Dec. 3, 2021 (CN) .......................... 202111472349.1

(51) Int. Cl.
*C12Q 1/70* (2006.01)
(52) U.S. Cl.
CPC .................................. *C12Q 1/708* (2013.01)
(58) Field of Classification Search
None
See application file for complete search history.

(56) References Cited

U.S. PATENT DOCUMENTS

| | | | |
|---|---|---|---|
| 9,885,092 B2 * | 2/2018 | Lowe | ................... C12Q 1/6825 |
| 9,890,433 B2 | 2/2018 | Schroder | |
| 10,047,407 B2 | 8/2018 | Norman et al. | |
| 10,253,365 B1 | 4/2019 | Doudna et al. | |
| 2019/0054467 A1 * | 2/2019 | Handique | ......... B01L 3/502738 |
| 2021/0139889 A1 * | 5/2021 | Chen | .................. G01N 33/5088 |
| 2022/0313796 A1 * | 10/2022 | In | ....................... A61K 31/7052 |
| 2022/0411780 A1 * | 12/2022 | Bratman | ................. C40B 40/06 |

FOREIGN PATENT DOCUMENTS

| | | | | |
|---|---|---|---|---|
| CN | 102199531 A | * | 9/2011 | |
| CN | 112080549 A | * | 12/2020 | ........... C12Q 1/6816 |
| CN | 114381550 A | * | 4/2022 | |
| WO | WO-2008074182 A1 | * | 6/2008 | ............. C12Q 1/708 |

OTHER PUBLICATIONS

Xiong, D. et al. (2020). Rapid detection of sars-Cov-2 with crispr-Cas12a. PLoS Biology, 18(12), e3000978-e3000978. (Year: 2020).*
Li, G., Wu, M., Li, J., Cai, W., Xie, Y., Si, G., Xiao, L., Cong, F., & He, D. (2021). Rapid detection of porcine deltacoronavirus and porcine epidemic diarrhea virus using the duplex recombinase polymerase amplification method. Journal of Virological Methods, 292, 114096-114096. (Year: 2021).*
Gong, J., Zhang, G., Wang, W., Liang, L., Li, Q., Liu, M., Xue, L., & Tang, G. (2021). A simple and rapid diagnostic method for 13 types of high-risk human papillomavirus (HR-HPV) detection using CRISPR-Cas12a technology. Scientific Reports, 11(1), 12800-12800. (Year: 2021).*
Li et al. 2020. CN 112080549 A. English Translation. (Year: 2020).*
Fang et al. 2011. CN 102199531 A. English Translation. (Year: 2011).*
Li et al. 2022. CN 114381550 A. English Translation. (Year: 2022).*
Jiaojiao Gong et al., A simple and rapid diagnostic method for 13 types of high-risk human papillomavirus(HR-HPV) detection using CRISPR-Cas12a technology, Scientific Reports, 2021, pp. 2-7, vol. 11, Issue 1.
Internation Search Report of PCT/CN2022/114122, Mailed Nov. 30, 2022.

* cited by examiner

*Primary Examiner* — Janet L Andres
*Assistant Examiner* — Carey Alexander Stuart
(74) *Attorney, Agent, or Firm* — True Shepherd LLC; Andrew C. Cheng

(57) ABSTRACT

A multi-target nucleic acid detection kit for human papillomavirus (HPV) typing includes a recombinase polymerase amplification (RPA) primer set, an enzyme and a buffer system for Cas12a-crRNA, and a reporter molecule that displays a signal. In the detection method, a multi-channel microfluidic chip is used as a carrier, and RPA primers are designed for corresponding regions of different HPV subtypes to allow isothermal amplification. A crRNA set is designed for amplicons of different subtypes. The crRNA recognizes an HPV target in a sample, and then activates the CRISPR-Cas12a and cuts a reporter group to release a signal, thereby achieving accurate detection on HPV subtypes. The detection method shows a high sensitivity, a low cost, and easy operations, and is expected to be widely used in the screening of HPV infection.

6 Claims, 17 Drawing Sheets
Specification includes a Sequence Listing.

MULTIPLEXED NUCLEIC ACID DETECTION KIT FOR HUMAN PAPILLOMA VIRUS (HPV) TYPING, AND DETECTION METHOD

CROSS-REFERENCE TO RELATED APPLICATIONS

This application is a continuation of International Patent Application No. PCT/CN2022/114122 with a filing date of Aug. 23, 2022, designating the United States, and further claims priority to Chinese Patent Application No. 202111472349.1 with a filing date of Dec. 3, 2021. The content of the aforementioned applications, including any intervening amendments thereto, are incorporated herein by reference.

CROSS-REFERENCE TO A SEQUENCE LISTING

This application includes a Sequence Listing submitted electronically as a text file named 5401SEQ-list.xml, created on Nov. 16, 2023, with a size of 25,362 bytes. The Sequence Listing is incorporated by reference herein.

TECHNICAL FIELD

The present disclosure belongs to the technical field of nucleic acid detection, and specifically relates to a kit and method for detecting and typing human papillomavirus (HPV) subtypes. In the present disclosure, the detecting and typing the HPV types in a sample to be tested are achieved by joint use of a microfluidic chip, multiplex recombinase polymerase amplification (RPA), and multiplex clustered regularly interspaced short palindromic repeats (CRISPR)/CRISPR associated 12a (Cas12a).

BACKGROUND

Human papillomavirus (HPV) is a non-enveloped circular double-stranded DNA virus containing approximately 7,900 base pairs categorized into three gene regions: an early region (E region), a late region (L region), and an uncoding region (UCR) or an upstream regulatory region (URR). The E region has a total of 7 genes from E1 to E7 that are involved in the replication, transcription, translation regulation, and transformation of viral DNA. The E6 and E7 genes are main oncogenes of the HPV. The L region encodes a major coat protein L1 and a minor coat protein L2. HPV typing is mainly based on DNA homology of the L1 region, and thus primers are generally designed targeting this region during the HPV typing. The UCR has a replication origin of HPV genomic DNA and regulatory elements necessary for HPV expression.

Currently, there are more than 170 HPV subtypes that have been discovered, more than 40 of which can infect the genital cavity. In 1974, Zur Hausen proposed that HPV infection is closely related to cervical cancer. In 1995, the World Health Organization (WHO) and International Agency for Research on Cancer (IARC) identified HPV as the cause of cervical cancer. The HPV subtypes are divided into high-risk and low-risk types. The high-risk types include HPV 16, 18, 31, 33, 35, 39, 45, 51, 52, 56, 58, 59, 68, 26, 53, 66, 73, 82, and other types, among which the HPV 16 and HPV 18 are the most common genotypes globally, accounting for approximately 70% of all invasive cervical cancer cases. The low-risk types include HPV 6, 11, 40, 42, 43, 44, 54, 61, 81 and other types, which mainly cause condyloma acuminata.

It needs to be emphasized that humans infected with HPV do not necessarily catch diseases and have obvious symptoms. Since the body's immune system can clear HPV, most genital tract HPV infections may not produce clinical symptoms and are transient. According to statistics, about 90% of HPV infections may disappear within 2 years, and the specific time of disappearance is mainly determined by the HPV type of infection. The low-risk types disappear quickly (about 5 to 6 months), while the high-risk types may take 8 to 24 months to disappear. A small number of HPV-infected people cannot eliminate HPV in their bodies and cause clinically visible genital warts and squamous intraepithelial lesions. If a female continues to be infected with HPV, she may eventually develop cervical cancer. Since different HPV subtypes have different degrees of harm, timely screening, identification, and control are required. HPV vaccine, referred to as cervical cancer vaccine, currently has three main types: bivalent, quadrivalent, and nonavalent vaccines. The HPV vaccine is the first human vaccine to prevent malignant tumors and can prevent cervical cancer as well as other cancers and diseases caused by the HPV infection. Vaccination with the bivalent cervical cancer vaccine (targeting HPV 16/18) can greatly reduce a female's risk of developing cervical cancer in the future. The quadrivalent cervical cancer vaccine adds two low-risk subtypes of HPV 6/11 to HPV 16/18, thereby preventing more HPV infections. This type of vaccine can not only reduce the risk of cervical cancer, but also prevent common sexually-transmitted diseases and skin diseases in male and female, because the low-risk HPV subtypes can also cause exophytic condyloma-like lesions, flat condyloma-like lesions, and low-grade cervical intraepithelial neoplasia in the perianal skin of the genital tract and lower part of the vagina. The nonavalent cervical cancer vaccine adds five subtypes of HPV 31/33/45/52/58 belonging to the high-risk group on the basis of the quadrivalent vaccine, and is currently the most powerful cervical cancer vaccine.

The incidence of cervical cancer ranks second only to breast cancer among female malignant tumors in the world. There are approximately 500,000 new cases of cervical cancer annually, ⅓ of which are deaths, and more than 90% of cervical cancers are caused by HPV infection. In addition to the timely injection of cervical cancer vaccine mentioned above, the detection of HPV is also of great significance and urgent. Not only that, since different HPV subtypes show different pathogenic mechanisms, carcinogenic risks, and prognosis after infection, the typing and detecting of HPV subtypes can be conducted to assist clinical diagnosis and treatment.

Traditional early screening of cervical cancer mainly relies on cervical cytology, colposcopy, and histopathological examination. These techniques may easily lead to the detachment of diseased cells during cervical cell sampling, and the diseased cells may change their appearance or be covered by inflammatory cells and blood cells during the cell sample production. Moreover, the determination of results relies on the doctor's personal experience, thereby easily leading to missed diagnosis of the disease. Nowadays, there are also some modern molecular detection technologies. At present, the Food and Drug Administration (FDA, USA) has approved four kinds of detection products for cervical cancer-related high-risk HPV subtypes, namely Hybrid Capture 2 based on hybrid capture, Cervista HPV based on enzyme digestion signal amplification, Cobas HPV based on real-time fluorescence PCR, and Aptima HPV based on loop-mediated isothermal amplification (LAMP). However, these products all have cumbersome operations, low detection throughput, and limited identification of subtypes. Specifically, the PCR requires variable temperatures to amplify nucleic acid targets, and a thermal cycler is an essential piece of equipment. Due to a large size and a high cost of the thermal cycler, its application scenarios are subject to certain limitations (for example, it is difficult to popularize the thermal cycler in primary hospitals, clinics, and on-site diagnosis scenarios). In addition, PCR detection is generally based on fluorescence. Due to the common overlap of emission wavelengths among fluorophores, it is difficult to detect more than 6 targets solely by distinguishing different fluorescence during the actual detection. Accordingly, the PCR is difficult to achieve the integrated and high-throughput detection of more HPV subtypes. The LAMP is a constant-temperature amplification technology, with amplification of targets being completed only at 65° C., which is beneficial to simplifying a detection system. However, the amplification of a single target by LAMP generally requires designing three pairs of primers, such that the design of LAMP primers is relatively complicated. In particular, a larger number of targets can further increase the difficulty of primer design and the complexity of primers. Multiple studies in recent years have shown that LAMP-based detection methods are excessively sensitive and susceptible to interference from aerosols, and then have a high probability of cross-contamination, leading to widespread false positive and false negative results.

Recombinase polymerase amplification (RPA) technology is another type of isothermal amplification that has emerged in recent years. The target of this technology generally only needs to be amplified at around 37° C. within 15 min, thereby achieving single-molecule nucleic acid detection. The RPA has extremely low requirements for hardware equipment and is suitable for amplification of longer target sequences. Therefore, this technology has played an important role in different fields such as clinical medicine, laboratory medicine, molecular biology, genomics, and food safety, especially in the detection of microorganisms such as pathogenic bacteria and viruses. However, although RPA has a relatively simple amplification method, there is generally a risk of failure in primer design during the RPA. Unlike traditional PCR, the RPA cannot obtain suitable primers with a high probability to successfully amplify the target only based on primer design principles. There is also a general rule for RPA primer design. For example, a primer length is generally 30 nt to 35 nt; it should avoid polyguanine for the first 3 to 5 nucleotides at the 5'-end; it will benefit the amplification performance if the first 3 nucleotides at the 3'-end are guanine and cytosine since it can help the stable binding of the polymerase. Long strings of polypurines or polypyrimidines are avoided in primers as possible, and an excessively high (70%) or low (30%) GC content is not conducive to RPA amplification. In addition, when designing primers, secondary structure formation, primer-primer interaction, and hairpin structure sequences should be avoided as much as possible to minimize the formation of primer dimers. However, even with the guidance of the above primer design rules, there is still no software specifically for primer design. Effective primers mainly rely on a large number of synthesis and screening. So far, the amplification performance and efficiency of primers cannot be determined based on the sequences alone, such that it is generally necessary to pre-test and further screen candidate primers. In particular, the detection of multiple targets requires more tests to ensure that each target can be successfully amplified. Furthermore, when typing subtypes with highly similar sequences, it especially takes more time to optimize primers. The reason is that it is necessary to successfully amplify the corresponding target while avoiding cross-interference between similar targets. The manufacturers of the most widely used RPA commercial kit in the world currently point out in their product (a DNA amplification kit) analysis design manual: "Oligonucleotides of different sequences behave differently in reactions, but there are no fixed rules for predicting the performance of a specific amplification primer based on the order and composition of nucleotides"; and "Even small changes in an oligonucleotide sequence can sometimes lead to significant changes in primer activity". It can be seen that many attempts must be made to obtain RPA primers with desirable amplification effects.

RPA primer screening mainly includes the following steps: target region selection, candidate primer design, target amplification and detection, and re-screening based on results. It is worth mentioning that the selection of RPA target regions also has corresponding requirements. That is, a template sequence with a relatively "average" nucleotide composition is selected to the greatest extent, with a GC content of 40% to 60%, and long strings of polypurines or polypyrimidines and repetitive elements in the genome are avoided; moreover, forward/reverse repeated sequences and palindrome sequences are avoided to the greatest extent. In view of this, although the RPA method has many advantages and is widely used in single-target amplification and detection, it is rare to truly achieve multi-target (≥3) amplification and detection. For example, recently reported documents that can amplify 3 to 4 targets simultaneously include: Foods, 2020, 9, 278; Biosensors and Bioelectronics, 2021, 189, 113328; and Biosensors and Bioelectronics, 2021, 182, 113167. Indeed, in there is a document (Scientific Reports, 2021, 11, 12800) reporting that 13 HPV subtypes were detected based on RPA. However, the authors clearly mentioned in the article that only 3 of the 13 pairs of primers designed could be amplified normally, while the other primers showed extremely poor amplification efficiency or could not be amplified. At the end of this article, the primer design of RPA was adjusted with reference to PCR primer design to achieve amplification and detection of the corresponding HPV subtypes. However, the amplification and strict typing of HPV subtypes in samples still had not been truly achieved (two or more subtypes might appear simultaneously in clinical patient samples); on the contrary, after a sample was determined to be a single subtype through PCR detection, the corresponding primers were then added for amplification. That is, a possibility of primer cross-amplification of non-targets was not tested when multiple subtypes were present in the sample.

To sum up, it is still highly difficult to truly realize multi-target (>4) amplification and detection by RPA. In addition to the above primer design and target region selection, it also needs to pay attention to a total amount of primers in the RPA reaction when conducting multi-target amplification. As long as more than two amplification primers are used in the reaction, the amounts of different primers should be controlled and optimized, otherwise primer aggregation may easily occur to cause amplification failure. The HPV has dozens of subtypes, and there are more than ten common high-risk subtypes. It is of great significance to establish a simple, rapid, and sensitive method for typing HPV subtypes.

CRISPR/Cas, as an adaptive immune system of bacteria or archaea, can cut foreign genes to avoid the invasion by phages, viruses, or external plasmids. CRISPR RNA (crRNA) in the CRISPR-Cas12a system is used to recognize a target nucleic acid and then cleave a non-target nucleic acid (as a reporter molecule). A variety of in vitro detection methods have been developed (*Biosensors and Bioelectronics*, 2021, 187, 113292; *Nature Reviews Molecular Cell Biology*, 2019, 20,490), all of which show that this technology shows high sensitivity, accurate detection, and easy operation. By further combining this technology with techniques such as isothermal amplification, the target nucleic acid at levels as low as $10^{-18}$ M can be detected in a non-laboratory environment. However, for multi-target detection, especially for subtypes whose target sequences are relatively close, special attention needs to be paid when designing crRNA to avoid crRNA designed for one subtype from cross-recognizing another subtype, causing erroneous detection. Therefore, the design of crRNA for HPV subtypes must not only meet some requirements of the crRNA itself, but also ensure its high specificity. Accordingly, certain difficulties need to be overcome to achieve the expected goals. In addition, microfluidic chips have low sample consumption, high throughput, and easy integrated operation. These chips can help automate the detection and has been widely used in the field of in vitro diagnostics.

SUMMARY OF PRESENT INVENTION

An objective of the present disclosure is to overcome the defects or deficiencies of the existing HPV detection technology, such as complex instruments, cumbersome operations, high cost, and difficulty in multi-target detection. The present disclosure provides a kit and a method for rapid and low-cost detecting and typing HPV subtypes. In the present disclosure, specific regions of HPV subtypes are found through researches, and can not only distinguish different subtypes, but also meet the design requirements of RPA primers and crRNA of CRISPR-Cas12a. In this way, the combination of RPA, CRISPR-Cas12a, and a microfluidic chip enables highly-sensitive, high-precision, and low-cost detecting and typing HPV subtypes. This method has simple operations, small sample consumption, high analysis speed, and no requirement on expensive instruments, and is suitable for screening and diagnosis of HPV infection in various medical institutions, especially primary hospitals and clinics.

To achieve the above objective, the present disclosure adopts the following technical solutions:

The present disclosure provides a kit for detecting and typing HPV subtypes, including an RPA primer set, a Cas12a protein, a crRNA set, and a reporter molecule, where RPA primers in the RPA primer set have nucleotide sequences shown in SEQ ID NO: 1 to SEQ ID NO: 18, and crRNAs in the crRNA set have nucleotide sequences shown in SEQ ID NO: 19 to SEQ ID NO: 27.

Further, the kit further includes a multi-channel microfluidic chip, where the multi-channel microfluidic chip has a sample injection well at a center, the sample injection well is connected to one end of each of multiple microchannels, and the other end of each of the multiple microchannels is connected to an outlet well. The microfluidic chip can be used as a carrier for the amplification, and its spatial distribution can be used to complete fluid diversion and identification of HPV subtypes. A substrate of the microfluidic chip is hydrophobically modified to prevent a reagent solution from flowing back to an inlet well when the outlet well is preloaded with a reagent. The outlet well can also be pre-loaded with a lyophilized reagent (such as Cas protein and crRNA) to facilitate transportation and storage.

Further, the reporter molecule is a biochemical molecule capable of promoting a signal change in a reaction system before and after cleavage of the Cas12a protein, and includes a single-stranded DNA (preferably including 4 to 15 bases), a DNA hairpin structure, and a DNA G-triplex or a DNA G-quadruplex (such as PS2.M, PS5.M, telomeric G-quadruplex, cMYC G-quadruplex, BCL-2G-quadruplex, and TBA); and both ends of the reporter molecule are separately labeled with a fluorophore capable of conducting fluorescence resonance energy transfer (FRET), or are labeled with a fluorophore and a quencher, respectively, or are separately labeled with a group capable of being detected based on a test strip (such as a fluorophore and a biotin group), or are separately labeled with a molecule or a group capable of being detected electrochemically (such as methylene blue), or are separately labeled with a molecule, a group, or a micro-nanoparticle (such as gold nanoparticles) capable of being detected optically through surface plasma through preferably fluorescence detection.

Further, the kit further includes an amplification reaction solution and an enzyme digestion buffer (10 mM Tris, pH=7.9, 5 mM to 20 mM of magnesium ions, and 50 mM to 500 mM of sodium ions or 0.5 mM to 500 mM of potassium ions). Preferably, the RPA primer set has a total final concentration of preferably 0.5 μM to 1.5 μM, most preferably 1 μM during amplification.

A method for detecting and typing HPV subtypes using the kit includes: amplifying a sample to be tested using the RPA primer set; mixing a resulting amplification product separately with the Cas12a protein, the reporter molecule, and the crRNA of each HPV subtype to allow enzyme digestion; and detecting a HPV subtype based on a signal change in the reporter molecule.

Preferably, the amplification product is injected from the sample injection well of the multi-channel microfluidic chip and split into different outlet wells; and the amplification product is mixed with the Cas12a protein, the reporter molecule, and the crRNA of each HPV subtype that are preloaded in the outlet well, and then subjected to the enzyme digestion. Alternatively, the sample to be tested, the RPA primer set, and the amplification reaction solution are directly injected from the sample injection well of the multi-channel microfluidic chip and split into different outlet wells, and then mixed with the Cas12a protein, the reporter molecule, and the crRNA of each HPV subtype that are preloaded in the outlet well to allow the amplification and enzyme digestion.

In the present disclosure, the identification of HPV subtypes mainly involves three core parts. 1) Design of RPA primers: the regions in HPV gene sequences that can identify multiple subtypes are found, and then RPA primers are designed accordingly. This process needs to effectively amplify the corresponding subtype fragments without cross-amplifying non-target subtypes, and also needs to meet the crRNA design principles of downstream CRISPR-Cas12a. 2) CRISPR-Cas12a detection system: it is necessary to find an appropriate region in the amplified fragment regions of multiple subtypes to design a crRNA set. Since crRNA also has a possibility of cross-recognizing other targets (especially when there is a high nucleic acid sequence similarity between subtypes), and requires the presence of a PAM sequence (TTTN) upstream of its target recognition region, thereby requiring a large amount of alignment and optimization. 3) Divergent multi-channel microfluidic chip: on one hand, as a carrier of the reaction solution, the microfluidic chip isolates the detection of each subtype to each microchannel and reaction well of the chip through spatial distribution, to detect the corresponding subtype using position coordinates. Since the number of spatial positions is easy to adjust and design (unlike the method of simply relying on different fluorophores to obtain different target detection, which is susceptible to overlap between color bands), only one fluorescent reporter molecule is needed to achieve high subtype detection throughput. On the other hand, the microfluidic chip can significantly reduce the demand for samples and can also omit the transfer of amplification products, which is beneficial to reducing aerosols.

The beneficial effects of the present disclosure are as follows: (1) For HPV subtypes, RPA, a constant-temperature amplification technology, does not require a complex PCR instrument and only requires a simple heating device to achieve specific amplification of multiple targets while avoiding cross-amplification. (2) A crRNA set of CRISPR-Cas12a is designed according to the target sequences, and specific recognition of a target by the crRNA can further improve the specificity of the detection. Meanwhile, the Cas12a enzyme, as a main body for the cleavage of the reporter group, can amplify the signal during the detection, thereby greatly improving the sensitivity and specificity. (3) The combination of a divergent multi-channel microfluidic chip serves to shunt and provide a place for reaction and detection. The shunted flow can simplify the complexity of a reaction system, allowing each outlet well to load only one type of crRNA. The multiple outlet wells of the microfluidic chip serve as a kind of spatial encoding, one reporter molecule can detect multiple targets, and the detected targets can be easily expanded. Compared with multi-target detection (fluorescence encoding) using a variety of fluorescent molecules, this mechanism not only greatly simplifies the detection device, but also greatly improves the target flux and signal accuracy, without spectral overlap. (4) Unlike conventional nucleic acid detection, which amplifies and then detects, the amplification and detection reactions can be conducted on the chip at the same time, which is conducive to simplifying the operations and shortening a detection time. (5) Related reagents, such as Cas12a and crRNA, can be pre-loaded in the outlet wells and then freeze-dried, thus facilitating storage, transportation, and on-site use.

BRIEF DESCRIPTION OF THE DRAWINGS

FIG. 11 shows that a liquid injected from the sample injection well can be evenly distributed to the 30 outlet wells to achieve cleavage as confirmed by fluorescence analysis; where the HPV 16 plasmid is injected from the sample injection well, and the outlet well is preloaded with the crRNA and Cas12a;

DETAILED DESCRIPTION OF THE EMBODIMENTS

Reagents: a Cas12a protein was purchased from Guangzhou Magigen Biotechnology Co., Ltd.; an HPV L1 gene plasmid, primers, TBA11-FQ, and crRNA each were provided by Beijing Tsingke Biotech Co., Ltd.

Example 1: Design and Optimization of RPA Primers

Figure 1:
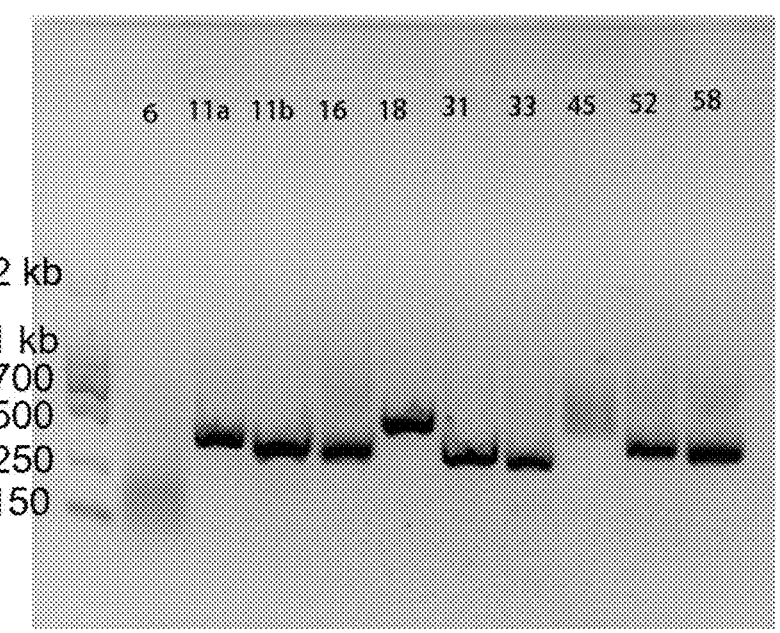
FIG. 1 shows amplification products of a first round of RPA primers for 9 HPV subtypes analyzed by PAGE.
Figure 2:
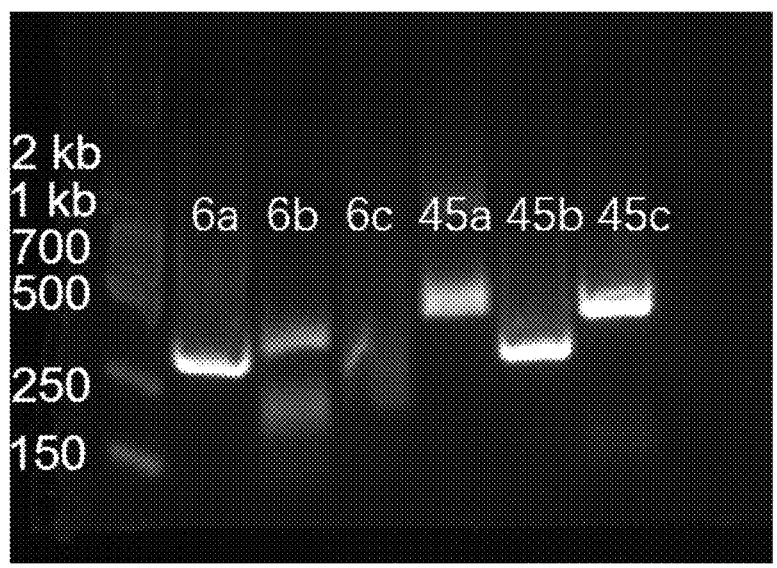
FIG. 2 shows a PAGE image of amplification products of a second round of primers for HPV 6 and HPV 45.
Figure 3:
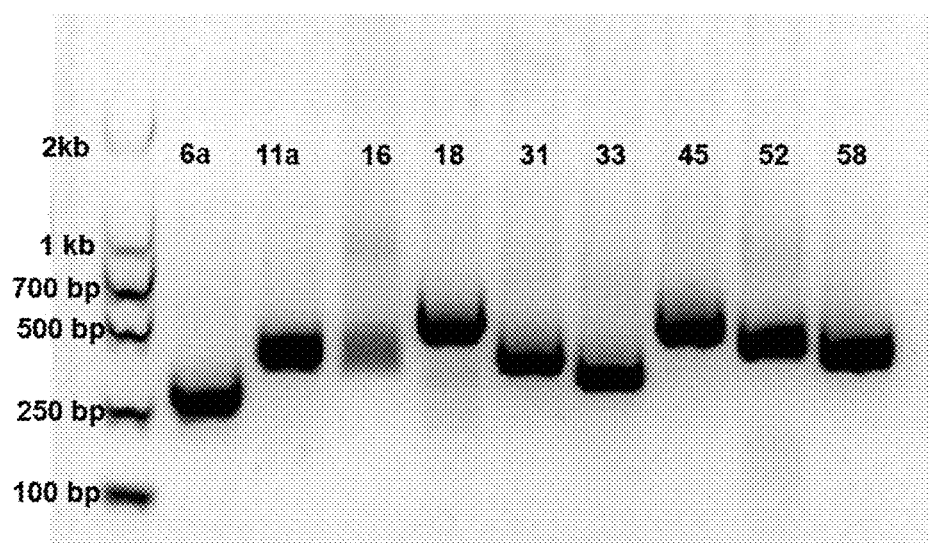
FIG. 3 shows PAGE images of RPA amplification products for 9 HPV subtypes.

In this example, corresponding regions on an L1 gene were found for genes of 9 HPV subtypes, and 10 pairs of RPA primers were designed accordingly (since HPV 11 and HPV 6 were highly similar in the primer design regions, in order to avoid possible cross-amplification and cross-recognition during subsequent detection, two pairs of primers were designed for HPV 11 as backup, as shown in Table 1). According to the instructions of an RPA kit (TwsitDx basic model), 9 HPV subtype targets were amplified (heated at 39° C. for 20 min), and then amplified products were analyzed by PAGE (FIG. 1). It was found that the primers of HPV 6 and HPV 45 were not ideal for template amplification. Therefore, based on the previously designed primers, three pairs of primers were designed for these two subtypes (Table 2). After PAGE analysis (FIG. 2), it was found that the primers HPV 6a and 6b had better amplification effects, but the amplification of HPV 6c failed; while all three primers of HPV 45 could be amplified normally. After comprehensive consideration, the forward and reverse primers of HPV 6b and HPV 45a were selected for multi-target amplification. The 9 pairs of primers finally selected were shown in SEQ ID NO: 1 to SEQ ID NO: 18, and the PAGE image of the amplified product was shown in FIG. 3. It was seen that RPA primers should be designed according to its rules as much as possible, and secondly, subtypes with insufficient amplification efficiency of the initial primers should be re-optimized. It could be even considered that several more pairs of primers were designed during optimization and a pair with better overall effects was selected for downstream experiments. Of course, sometimes it was necessary to re-select and re-optimize primers based on the results of downstream experiments.

TABLE 1

RPA primer sequences designed for L1 region of 9 HPV subtypes

| | |
|---|---|
| HPV 6 Forward | Not shown due to unselected |
| HPV 6 Reverse | Not shown due to unselected |
| HPV 11 Forward a | Not shown due to unselected |
| HPV 11 Reverse a | Not shown due to unselected |
| HPV 11 Forward b | CCTTTAGGCGTTGGTGTTAGTGGGCATCCATTG (SEQ ID NO:3) |
| HPV 11 Reverse b | CATCCGATTTATTGGTTTGTAAGTCTGCAA (SEQ ID NO: 4) |
| HPV 16 Forward | CTGTCCCAGTATCTAAGGTTGTAAGCACGG (SEQ ID NO: 5) |
| HPV 16 Reverse | CTAATGGCTGACCACGACCTACCTCAACAC (SEQ ID NO: 6) |
| HPV 18 Forward | CACTGGGCTAAAGGCACTGCTTGTAAATCG (SEQ ID NO: 7) |
| HPV 18 Reverse | CAACTGGGAGTCAGAGGTAACAATAGAGCC (SEQ ID NO: 8) |
| HPV 31 Forward | CTGTCCCAGTGTCTAAAGTTGTAAGCACGG (SEQ ID NO: 9) |
| HPV 31 Reverse | CACTAATACCTACACCTAATGGCTGCCCGC (SEQ ID NO: 10) |
| HPV 33 Forward | CTTGAAATAGGTAGAGGGCAGCCATTAGGC (SEQ ID NO: 11) |
| HPV 33 Reverse | CCTCAATAATAGTATTTATAAGTTCTAAAGGTGG (SEQ ID NO: 12) |
| HPV 45 Forward | Not shown due to unselected |
| HPV 45 Reverse | Not shown due to unselected |
| HPV 52 Forward | CCTGTCTCTAAGGTTGTAAGCACTGATGAG (SEQ ID NO: 15) |
| HPV 52 Reverse | CCCACTAATACCCACACCTAAAGGCTGTCC (SEQ ID NO: 16) |
| HPV 58 Forward | CTCCTGTGCCTGTGTCTAAGGTTGTAAGCA (SEQ ID NO: 17) |
| HPV 58 Reverse | CCAATGGCTGTCCTCTACCTATTTCAAGGC (SEQ ID NO: 18) |

TABLE 2

Second round of primer design for HPV 6 and HPV 45

| | |
|---|---|
| HPV 6 Forward a | Not shown due to unselected |
| HPV 6 Reverse a | Not shown due to unselected |
| HPV 6 Forward b | CAGCCATTAGGTGTGGGTGTAAGTGGACATCC (SEQ ID NO: 1) |
| HPV 6 Reverse b | Not shown due to unselected |
| HPV 6 Forward c | Not shown due to unselected |
| HPV 6 Reverse c | CTGGTAATAAGTTCTAAGGGCGGGCAGTCACC (SEQ ID NO: 2) |
| HPV 45 Forward a | CCCTTCTCCCAGTGGCTCTATTATTACTTC (SEQ ID NO: 13) |
| HPV 45 Reverse a | CCAAACTTGTAGTAGGTGGTGGAGGGACAC (SEQ ID NO: 14) |
| HPV 45 Forward b | Not shown due to unselected |
| HPV 45 Reverse b | Not shown due to unselected |
| HPV 45 Forward c | Not shown due to unselected |
| HPV 45 Reverse c | Not shown due to unselected |

Example 2: Optimization of Primer Concentration

Figure 4:
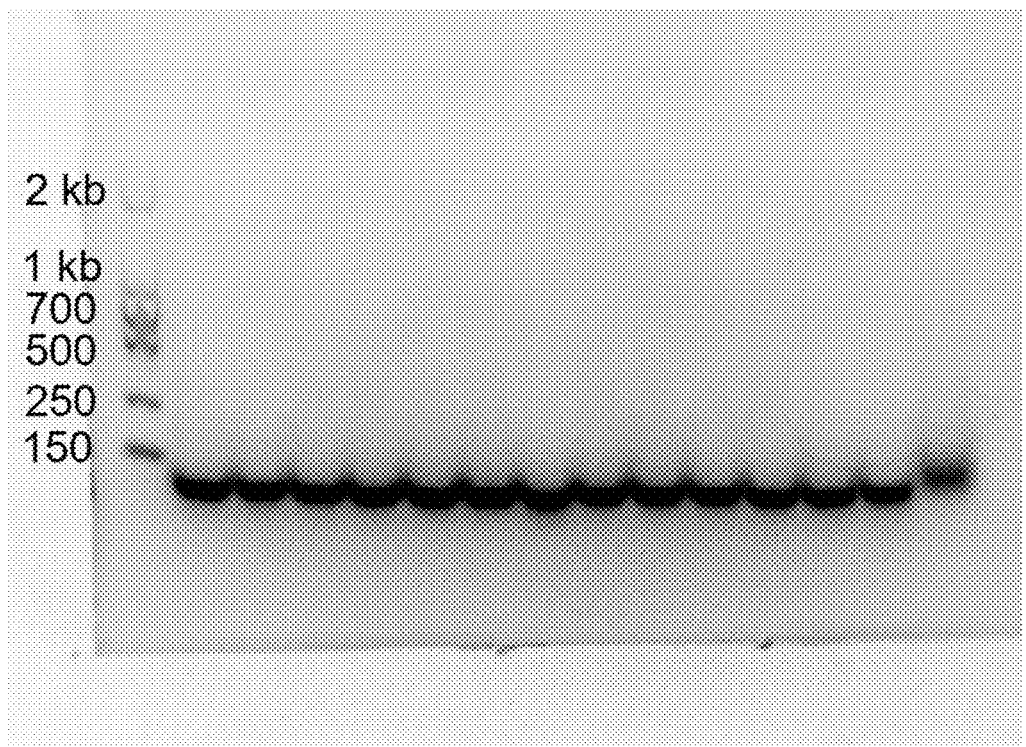
FIG. 4 shows amplification results when there are 9 HPV subtypes (where 14 bands are individual 9 subtypes, some mixed subtypes, and a blank control) and RPA primers have a total concentration of 10 μM; and a bottom band should be a primer-dimer band.
Figure 5:
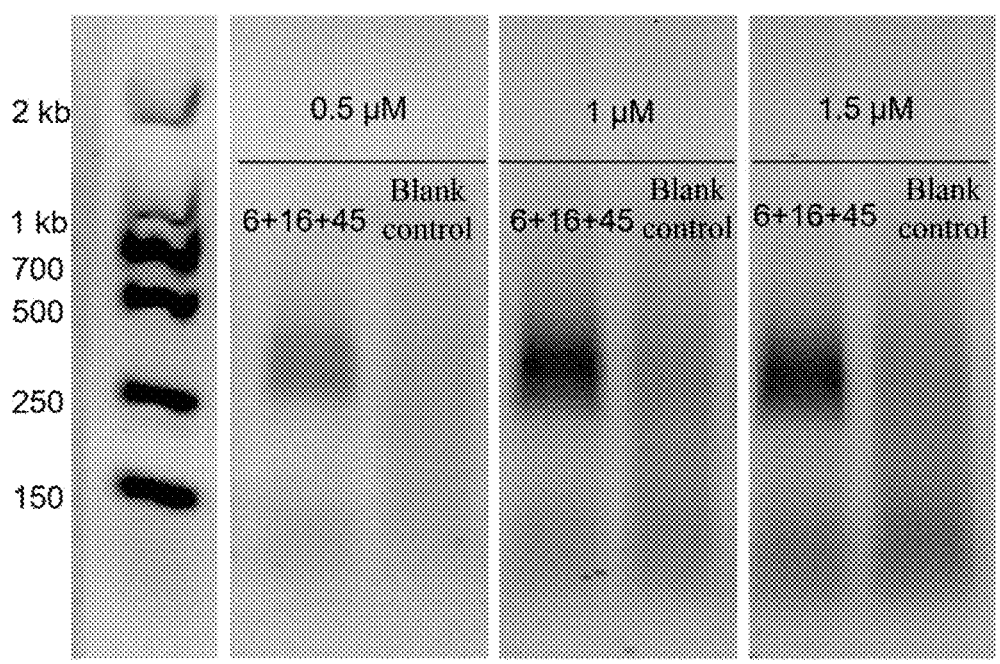
FIG. 5 explores concentrations of the RPA amplification primers for three subtypes of plasmids, where 0.5 μM, 1 μM, and 1.5 μM are total primer concentrations in several sets of amplification experiments, respectively.

Studies had shown that when conducting multi-target RPA amplification, whether the primer concentration was appropriate directly affected a final effect. For example, when there was only one target in the amplification system, the final primer concentration was generally 1 µM; however, when there were more than 2 targets, the total primer concentration could not be directly increased by the corresponding multiple, but should be adjusted appropriately. As shown in FIG. 4, when the final concentration of total primers in the amplification reaction system was excessively high (10 µM), primer dimers might be formed, causing amplification failure. Further, the primer concentration was explored. It was speculated that even if there were more targets to be amplified, the total primer concentration might only need to be equivalent to the total primer concentration present for a single target. Therefore, the final total primer concentrations were selected as 0.5 µM, 1 µM, and 1.5 µM, respectively. The target was a combination of three subtypes: HPV 6, HPV 16 and HPV 45 (in addition to exploring the primer concentration, target typing could also be conducted later to test the specificity), primers were a mixture of primers corresponding to these three subtypes, and RPA amplification was conducted. As shown in FIG. 5, all three primer concentrations could achieve amplification. However, when the primer concentration was 0.5 µM, a product concentration was relatively poor; when the primer concentration was 1.5 µM, although the product concentration was higher, some primer-dimer bands appeared at the bottom of the lane. As a result, based on these results, 1 µM was preferred as a total primer concentration during the amplification.

Example 3: Design and Optimization of crRNA for 9 HPV Subtypes

After the target nucleic acid was amplified by RPA, the target was detected by CRISPR. Specifically, since the CRISPR-Cas12a system could activate a trans-cleaving activity of crRNA after pairing with the target, a reporter molecule dual-labeled with fluorophore and quencher was cleaved, thereby releasing strong fluorescence for detection.

The present disclosure was aimed at the detection of HPV subtypes, and for each target amplification region, multiple alternative sequences were found that complied with the basic principles of crRNA design (that is, the target chain contained a PAM sequence "TTTN"). It was checked whether the 20 nucleotides after the PAM sequence did not contain "AAA". Based on this, 5 crRNAs targeting HPV 16 were selected between 5685 to 5993 on the L1 gene. Then the sequences of these 5 crRNAs were compared with the other 8 HPV subtypes, and it was ensured that in addition to the 3'-end, there were at least three different bases from other subtypes to find out crRNA1 and crRNA5 from the 5 crRNAs to meet this requirement. Moreover, considering that the crRNA 1 was more different from other subtypes, the crRNA 1 was preferred while the crRNA 5 was used as a backup. In addition, since crRNA was designed and recognized for the amplified region, crRNA design and the primer design mentioned above also needed to be considered comprehensively. For example, as mentioned earlier, when designing RPA primers for HPV 6 subtype in the first round, it was found that the amplification effect was not desirable, so three pairs of primers for HPV 6a, HPV 6b, and HPV 6c were designed in the second round. Among them, the HPV 6c showed a poor amplification effect, while the HPV 6a and HPV 6b showed a better amplification effect. However, it was found that the L1 gene fragment between the forward and reverse primers of HPV 6a could not be designed to meet the above requirements, such that HPV 6b was finally selected.

Figure 6:
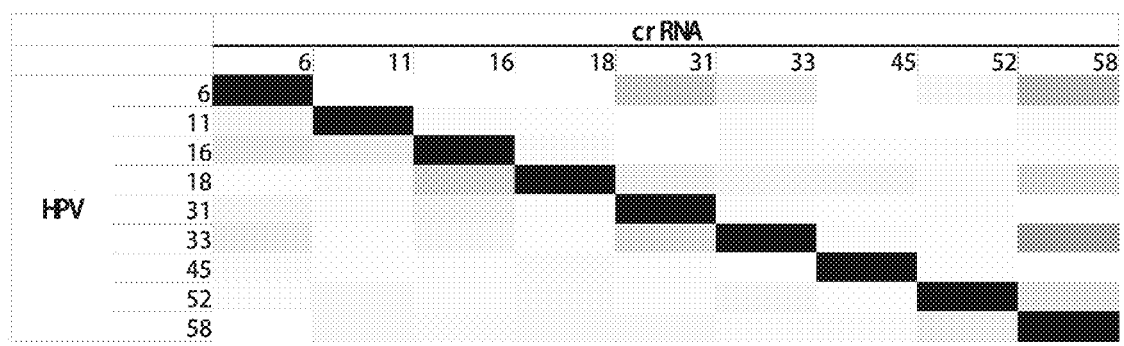
FIG. 6 shows that 9 crRNAs and 9 subtypes are cross-tested in a matrix form to verify a specificity of the designed crRNA.

After determining the crRNA of each subtype, a 9×9 orthogonal experiment was conducted to verify the recognition effect. In a 96-well plate, 1 μL of Cas12a (2 μM) and 27 μL of buffer (10 mM Tris, pH=7.9, 70 mM KCl, 10 mM $MgCl_2$) were separately mixed with 2 μL of crRNA (1 μM) of HPV 6, HPV 11, HPV 16, HPV 18, HPV 31, HPV 33, HPV 45, HPV 52, and HPV58 (3 replicate wells were configured for each subtype), and then incubated at 37° C. for 10 min. 10 μL of the L1 fragment (synthetic plasmid, 40 ng/μL) of HPV 61, HPV 1, HPV 16, HPV 18, HPV 31, HPV 33, HPV 45, HPV 52, and HPV58 and 10 μL of TBA11-FQ (100 μM) were added to the above system, and then incubated at 37° C. for 15 min. Thereafter, Cas12a was inactivated by heating at 65° C. for 10 min. A fluorescence value was measured with a microplate reader (excitation at 488 nm, collection at 500 nm to 600 nm), and then the fluorescence at 518 nm was taken out (average of 3 replicate wells for each subtype) to draw a graph. As shown in FIG. 6, when crRNA and the corresponding HPV subtype existed at the same time (i.e., on the diagonal), there is an extremely high fluorescence value; in other cases where the two were not corresponding, the fluorescence value was extremely low (although there were a few values that were slightly higher, and did not affect the determination). It was seen that the crRNA designed for 9 subtypes showed desirable specificity.

Figure 7:
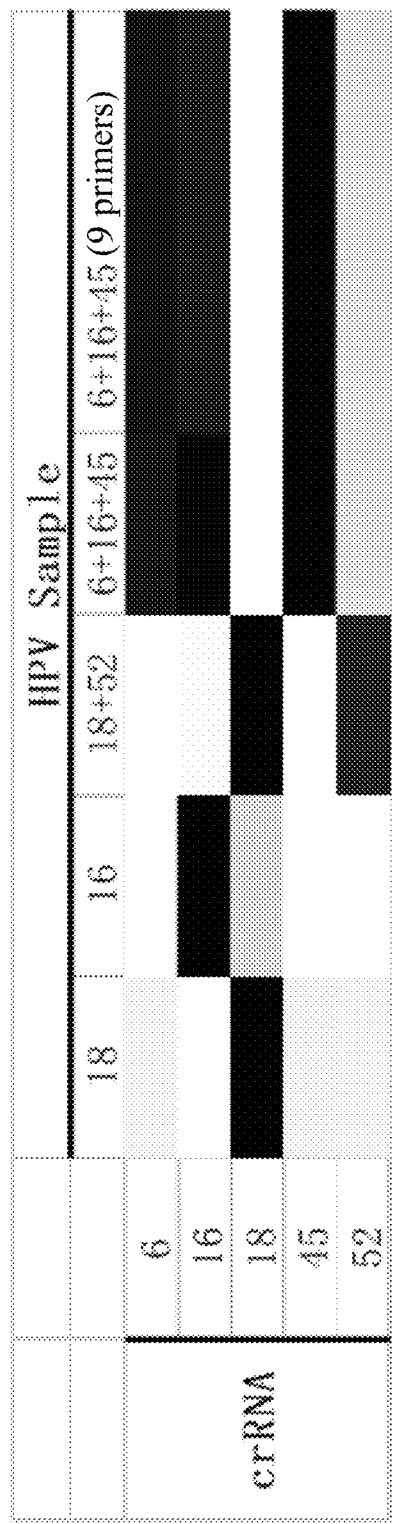
FIG. 7 shows simultaneous amplification and crRNA identification detection for 1 to 3 HPV subtypes.

In addition, samples containing 1, 2, and 3 HPV subtypes (these samples had been clinically tested for HPV typing by PCR) were further subjected to RPA amplification using corresponding 1, 2, and 3 or 9 primers (a total primer concentration for each amplification reaction was 1 μM), and then 9 types of crRNAs were selected for identification. As shown in FIG. 7, the fluorescence test results indicated that when the corresponding target existed in the reaction system, it could be specifically recognized by the corresponding crRNA. This result once again proved that the designed primers could accurately amplify HPV subtypes contained in clinical samples; and the designed crRNA could achieve high specificity recognition without obvious cross-recognition.

Figure 8:
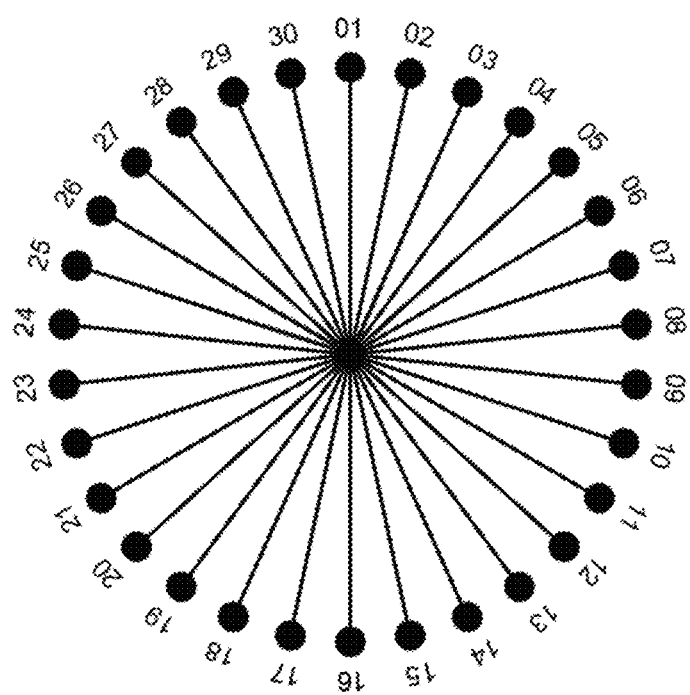
FIG. 8 shows the design of a divergent 30-channel microfluidic chip; where the chip includes a central sample injection well, 30 connecting channels, and 30 outlet wells.

Example 4: Design, Production, and Testing of Divergent Multi-Channel Microfluidic Chip In order to achieve efficient typing of HPV subtypes, a microfluidic chip was further introduced to combine with RPA amplification and CRISPR detection, and liquid shunting and reaction control were realized through the spatial layout of microchannels in the microfluidic chip. The introduction of microfluidics was highly important and was a key point to achieve efficient multi-target typing. Through the microfluidic chip, multiple outlet wells distributed at different positions in space corresponded to multiple subtypes of the sample to be tested. In this way, multiple targets could be detected using only one fluorescent reporter molecule, and a detection throughput could be easily increased. In conventional methods, fluorophores of different colors (color coding), or magnetic beads of different sizes or barcodes (size coding, barcoding) were generally used to identify different targets in order to achieve multiple target detection. Although these methods could achieve identification between targets, they had complex operations, low resolution between targets, difficulty in preparation, and high cost. In this example, the designed chip was a divergent 30-channel microchannel chip, as shown in FIG. 8. There was a sample injection well, 30 connecting channels, and 30 outlet wells designed in the middle of the chip; the outlet wells were numbered from 1 to 30 to achieve space coding. PDMS with microstructure was produced by classic soft photolithography, and the sample injection well and 30 outlet wells were punched correspondingly using a well punch (not all of the 30 outlet wells should be punched, and they could also be punched selectively according to experimental needs). Before attaching the PDMS with wells to a glass bottom plate, the glass bottom plate was subjected to a layer of hydrophobic modification: about 0.5 mL of Aquapel was added dropwise onto a washed and blown-dried glass plate (75 mm×50 mm×1 mm), applied evenly with a brush that came with the Aquapel, the glass plate was air-dried, and then excess Aquapel was wiped off with dust-free paper. This hydrophobic modification was simple, convenient, effective, and low-cost. Of course, other hydrophobic reagents could also be used to pretreat the glass bottom plate. The PDMS was then attached to the glass bottom plate.

Figure 9:
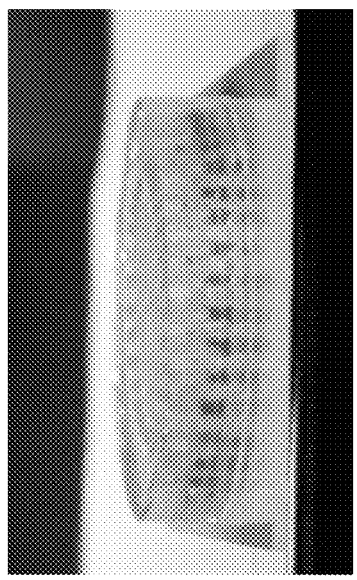
FIG. 9 shows photos taken at different angles after loading a pigment solution on the divergent 30-channel microfluidic chip.
Figure 9:
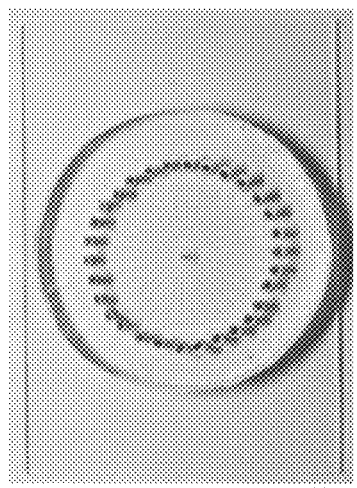
Figure 9:
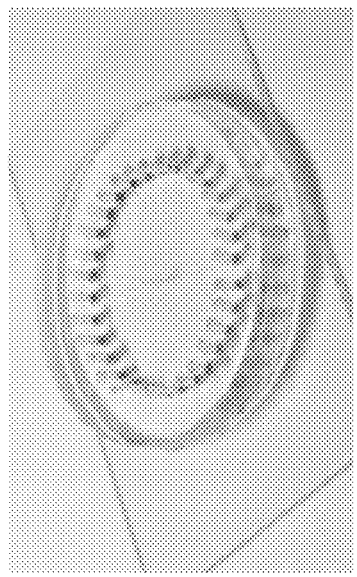
Figure 10:
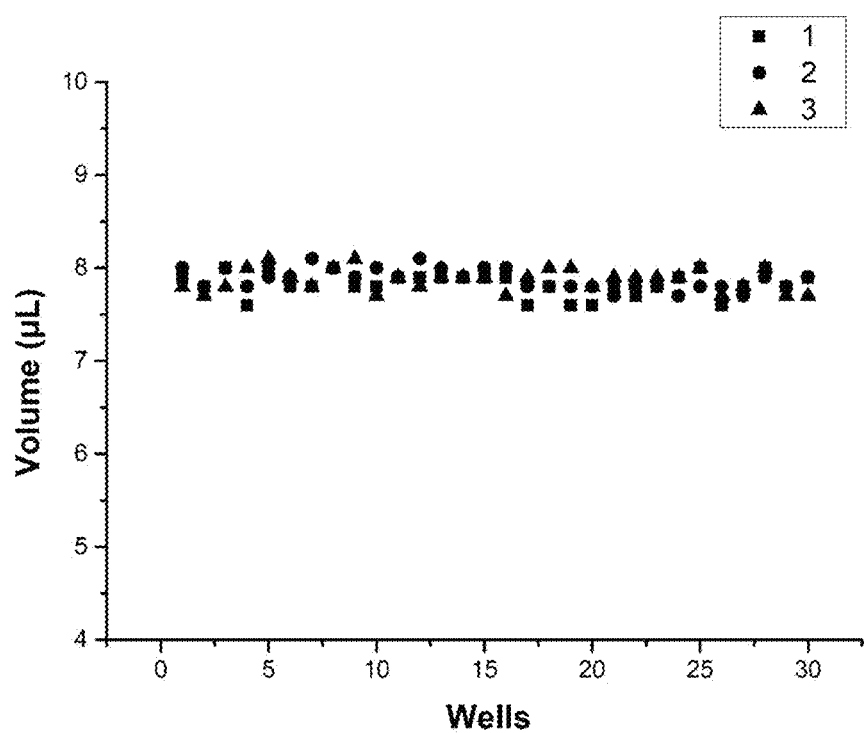
FIG. 10 shows a volume of solution obtained in each of the 30 outlet wells on the microfluidic chip after injecting 240 μL of the solution from the sample injection well 3 times.

It showed that a liquid injected from the sample injection well could be evenly distributed to the 30 peripheral outlet wells. Specific operations were as follows:

240 μL of ultrapure water dissolved with a green pigment was injected into the chip from the sample injection well with a syringe, and the liquid could be distributed to the 30 outlet wells on the periphery of the chip through 30 connecting channels (FIG. 9). The liquid from each well was carefully drawn with a micro-syringe and a volume was read through the syringe scale. The reading was repeated three times and the data was recorded as shown in FIG. 10. It was seen that the volume of each well was about 8 μL, indicating that the chip could achieve uniform distribution of liquid very well.

Example 5

Figure 11:
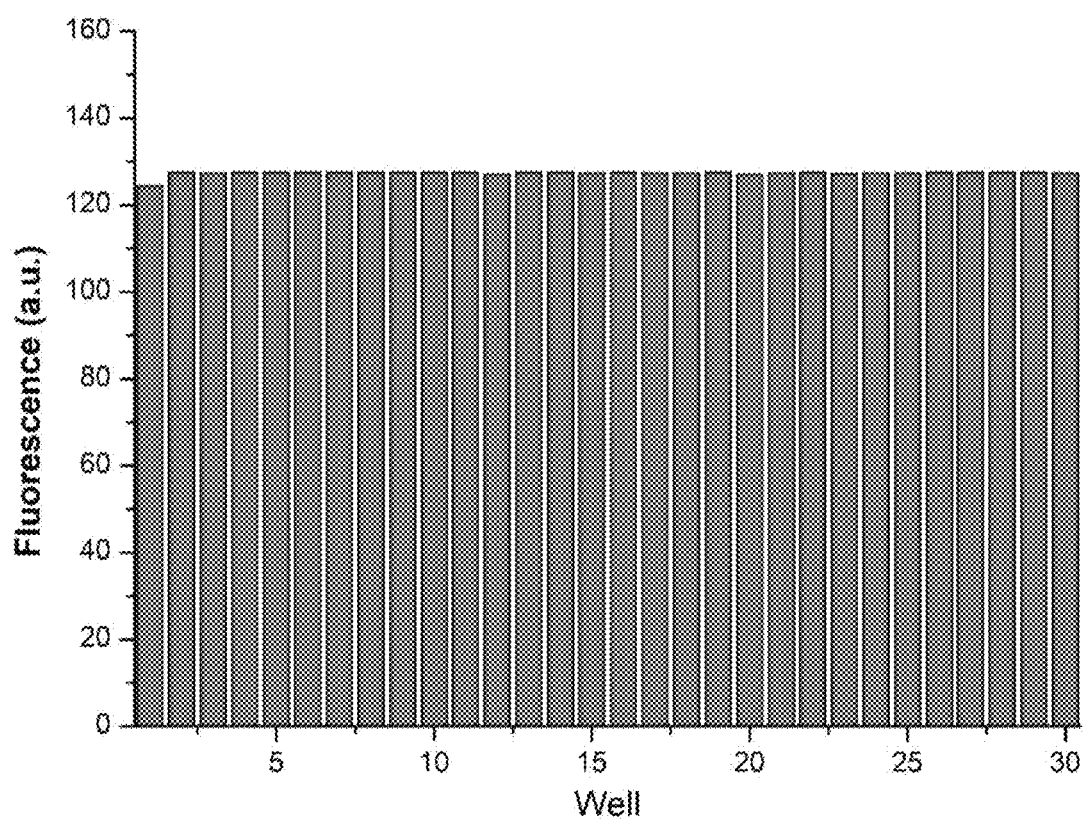

In this example, it was characterized that a reagent injected into the chip from the sample injection well could be fully mixed and reacted with a reagent pre-added to the outlet well. Specific operations were as follows:

The Cas12a (37.5 μL, 2 μM), HPV 16crRNA (75 μL, 1 μM), and 34.5 μL of a buffer were incubated at 37° C. for 10 min; TBA11-FQ (3 μL, 100 μM) was added to a resulting reaction system, mixed well, and then 4 μL of an obtained mixture was added to each of the 30 outlet wells. Due to the hydrophobic modification of the chip substrate, the solution in the outlet well did not flow back into the connecting channel or sample injection well. 120 μL of the HPV 16 DNA (40 ng/μL) was added from the central sample injection well with a syringe and shunted into each outlet well. Then the chip was placed in a constant-temperature metal bath (37° C., 15 min) on a temperature control device, and then taken out to collect the green fluorescence of each well under a microscope, and the fluorescence value was extracted using Image J. The results were shown in FIG. 11, which showed that the fluorescence values in the 30 outlet wells were extremely uniform (except for the first well, which showed slightly weaker fluorescence due to punching). This result further proved that the liquid injected from the sample injection well could be evenly distributed to each outlet well, and also proved that the reaction liquid in each well was fully mixed and reacted.

Example 6

Figure 12:
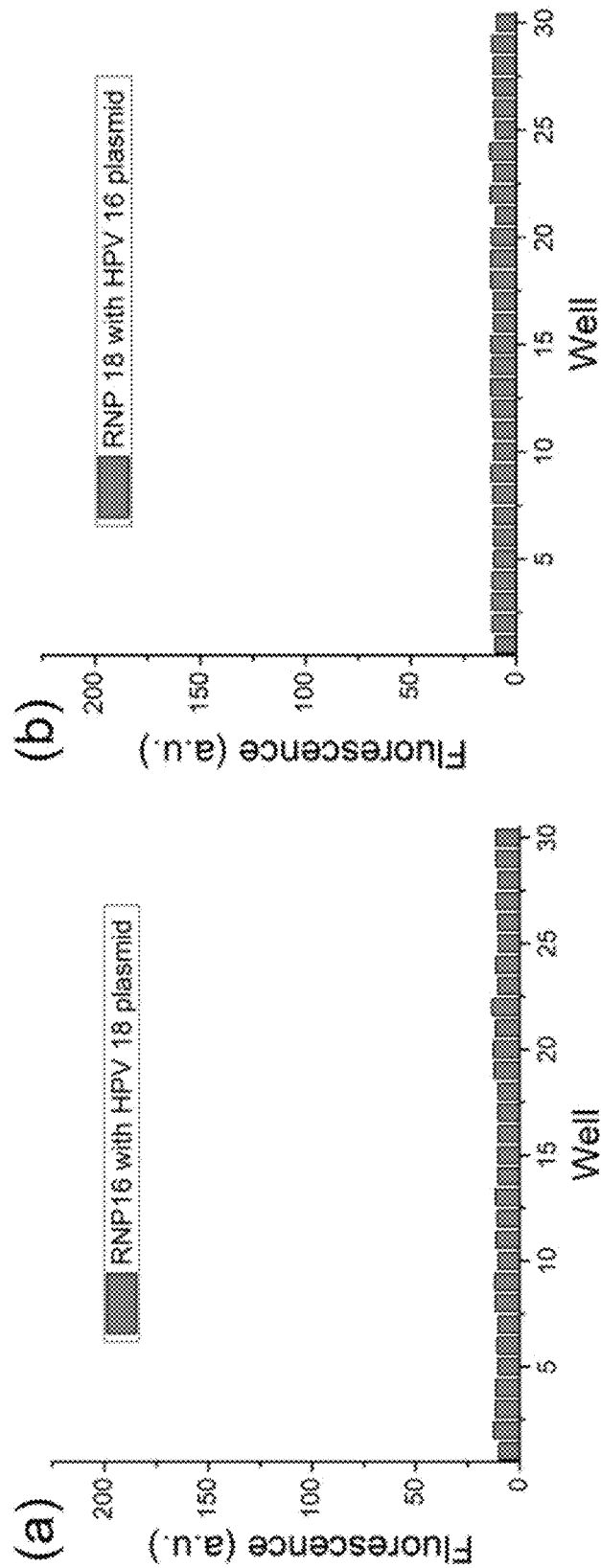
FIG. 12 confirms that there is no cross-recognition between crRNAs for the HPV 16 or HPV 18.

In this example, it was confirmed that the crRNA of HPV 16 and HPV 18 on the microfluidic chip did not cross-recognize non-corresponding targets. The specific operations were as follows:

The Cas12a (25 μL, 2 μM), HPV 16crRNA (50 μL, 1 μM), and 20 μL of a buffer were mixed and incubated at 37° C. for 10 min. TBA11-FQ (5 μL, 40 μM) was added to a resulting reaction system, mixed well, and an obtained mixture was added to the outlet wells 1 to 15 of the chip separately, at 4 μL per well. Meanwhile, TBA11-FQ (5 μL, 40 μM) was added with 95 μL of the buffer, and an obtained mixture was added into wells 16 to 30 separately, at 4 μL per well, as a negative control. A solution containing HPV 18 plasmid (120 μL, 40 ng/μL) was injected into the chip from the central sample injection well with a syringe, and the solution was divided into each outlet well; the chip was placed in a temperature control device for metal bathing (37° C., 15 min). After taking out, a green fluorescence photo of each well was taken under a microscope, and the fluorescence value was analyzed using Image J to draw a graph shown in FIG. 12a. The results showed that the fluorescence value in outlet wells 1 to 15 containing Cas12a+HPV 16crRNA (RNP16) was close to the fluorescence value in wells 16 to 30 of the negative control group. This indicated that no obvious cleavage events occurred in these outlet wells 1 to 15, proving that the crRNA of HPV 16 could not recognize the HPV 18 plasmid.

In the same way as the above solution configuration, whether RNP18 could recognize the HPV 16 plasmid was tested. The results were shown in FIG. 12b, indicating that the crRNA of HPV 18 could not recognize the HPV 16 plasmid.

The above results showed that there was no cross-recognition of non-corresponding subtypes by crRNA on the chip.

Example 7

Figure 13:
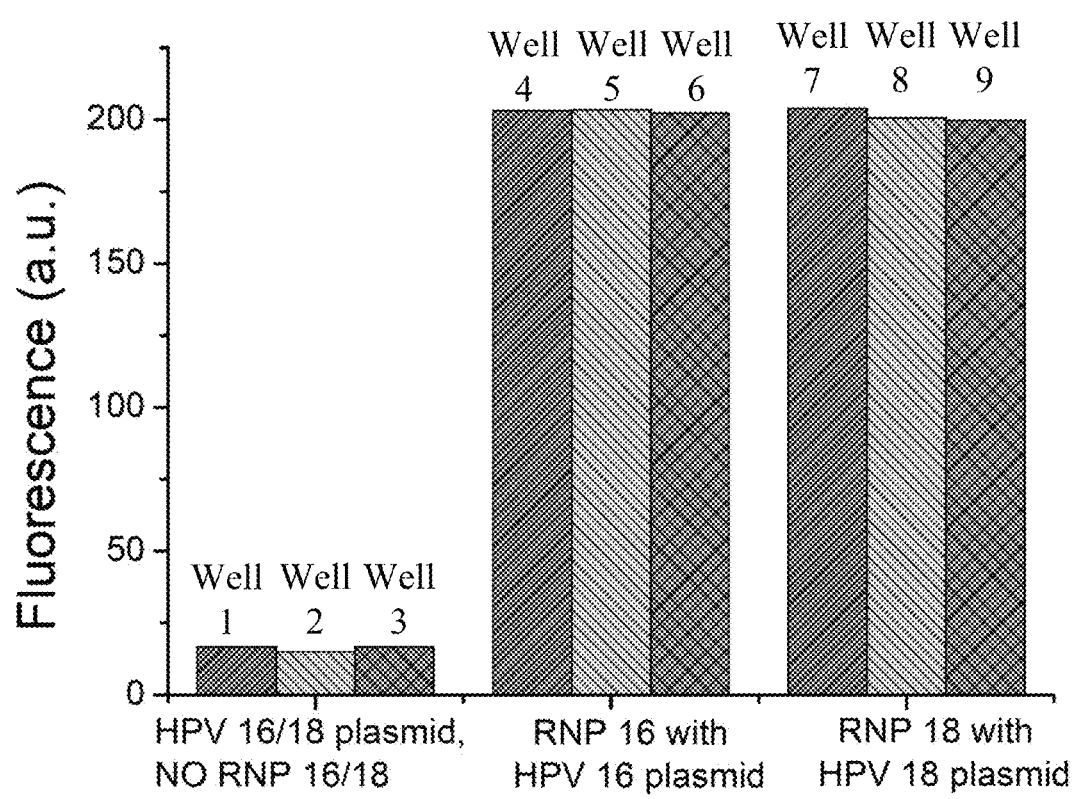
FIG. 13 confirms that the crRNA designed for HPV 16 or HPV 18 has a high specificity.

In this example, it was tested that the present disclosure could realize the typing of HPV 16 and HPV 18 on the microfluidic chip. Specific operations were as follows:

The Cas12a (5 μL, 2 μM), HPV 16crRNA (10 μL, 1 μM), and 5 μL of a buffer were incubated at 37° C. for 10 min. TBA11-FQ (1 μL, 40 μM) was added to a resulting reaction system, mixed well, and 4 μL of a resulting mixture was added to outlet wells 4 to 6 separately; similarly, a reaction solution containing Cas12a, HPV 18crRNA, and TBA11-FQ was prepared and added to outlet wells 7 to 9; TBA11-FQ (1 μL, 40 M) and 19 μL of the buffer were mixed, and 4 μL of a resulting mixture was added to outlet wells 1 to 3 separately, as a negative control. In this example, the outlet wells 10 to 30 were not punched. A solution containing HPV 16 (20 μL) and HPV 18 (20 μL) plasmids was injected into the chip from the central sample injection well with a syringe and shunted to the outlet wells. The chip was placed in a 37° C. constant-temperature metal bath for 15 min and taken out. A green fluorescence photo of each well was taken under a microscope, and the fluorescence values in outlet wells 1 to 9 were analyzed using Image J to draw a graph shown in FIG. 13. The results showed that the fluorescence value in negative wells 1 to 3 without RNP16/18 was extremely low; while the fluorescence values in wells 4 to 6 and 7 to 9 containing RNP 16 or 18 were much higher than those in the negative control wells. This proved that the two injected plasmids were accurately identified in the corresponding outlet wells.

This example and Example 6 collectively showed that the technical solution of the present disclosure could accurately realize the typing of HPVs 16/18 with a strong specificity.

Example 8

Figure 14:
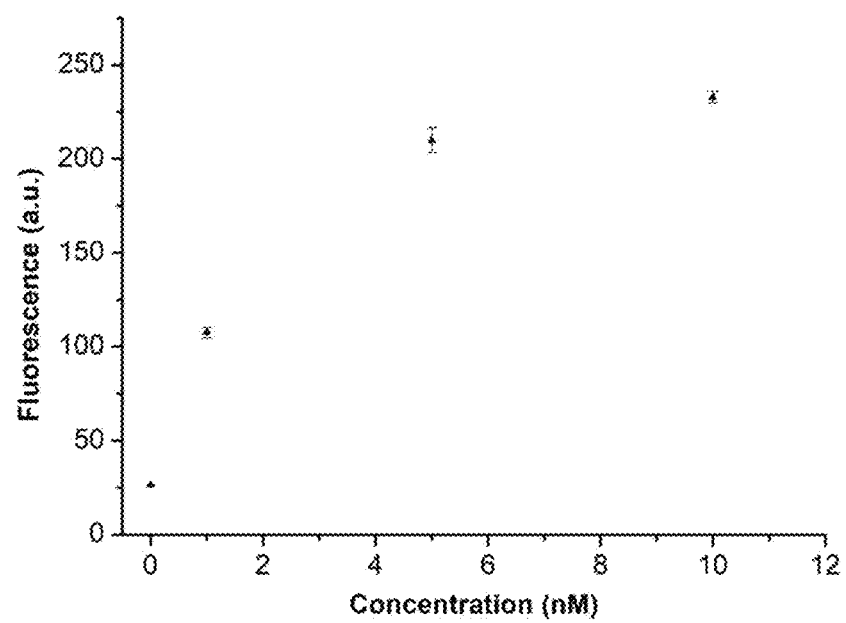
FIG. 14 shows that a fluorescence produced by a reaction system is stronger as a concentration of the HPV 16 plasmid increases.

In this example, it was characterized that the present disclosure could detect HPV plasmids at different concentrations. Specific operations were as follows:

The HPV 16 plasmid was diluted to different concentrations (10 nM, 5 nM, 1 nM, and 0 nM), and then these 4 concentrations of plasmid solutions were added to outlet wells 1 to 12 separately (3 wells for each concentration, at 4 μL per well), and the remaining outlet wells 13 to 30 were filled with 4 μL of a buffer to maintain uniform pressure distribution throughout the outlet wells of the chip when adding samples. The Cas12a (30 μL, 2 μM), HPV 16crRNA (60 μL, 1 μM), and 24 μL of the buffer were incubated at 37° C. for 10 min, then TBA11-FQ (6 μL, 40 μM) was added to a resulting reaction system. After mixing well, an obtained mixed solution was injected using a syringe into the chip from the central sample injection well and distributed evenly to the peripheral outlet wells. Then the chip was placed into a temperature control device for constant-temperature metal bathing (37° C., 15 min), taken out, and a green fluorescence photo of each well was taken under a microscope. The fluorescence values were analyzed using Image J, and the fluorescence values at four concentrations were averaged to draw a graph shown in FIG. 14. The results showed that the fluorescence value gradually increased as the concentration increased, confirming that the present disclosure could detect HPV DNA at different concentrations.

Example 9

Figure 15:
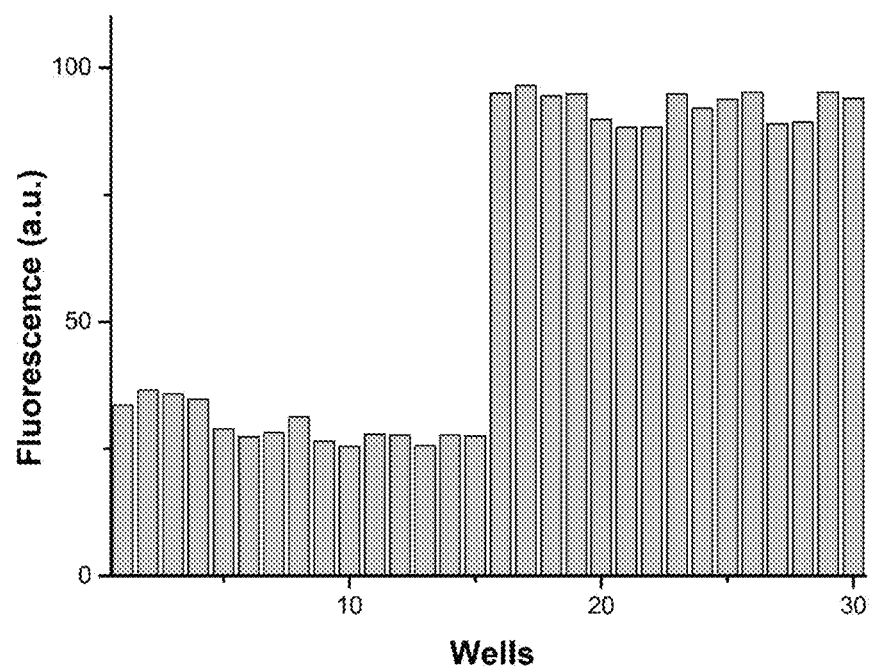
FIG. 15 shows fluorescence analysis results after amplification and detection on the chip; where an RPA amplification solution of the HPV 18 is injected into the sample injection well, outlet wells 1 to 15 are a control group without Cas12a and crRNA, and outlet wells 16 to 30 are the crRNA added with Cas12a and HPV 18 subtype.

For target detection, it is a conventional idea to amplify and then detect; if amplification while detection can be achieved at the same time, it may be possible to greatly simplify the operations and effectively shorten a detection time. In this example, it was characterized that the present disclosure could realize nucleic acid amplification and detection at the same time. Specific operations were as follows:

The Cas12a (25 μL, 2 μM), HPV 18crRNA (50 μL, 1 μM), and 20 μL of a buffer were mixed and incubated at 37° C. for 10 min; TBA11-FQ (5 μL, 40 μM) was added to a resulting reaction system, mixed well, and an obtained mixture was added to the outlet wells 16 to 30 separately, at 4 μL per well; meanwhile, TBA11-FQ (5 μL, 40 μM) was mixed with 190 μL of the buffer, and an obtained mixture was added into wells 1 to 15 separately, at 4 μL per well, as a negative control. An RPA reaction solution was prepared, including: A Buffer (40 μL), an enzyme reaction mixture (14 μL), a Forward primer (4 μL, 10 M), a Reverse primer (4 μL, 10 μM), 27 μL of pure water, B Buffer (5 μL), and HPV 18 plasmid (6 μL, 1 μM). This amplification reaction solution was injected into the chip from the central sample injection well at one time, and then the chip was placed in a 37° C. metal bath and incubated for 30 min. A green fluorescence photo of each well was taken under a microscope to allow fluorescence analysis, and the results were shown in FIG. 15. The results showed that the fluorescence in outlet wells 16 to 30 was much higher than the fluorescence value in outlet wells 1 to 15 of the negative control. This confirmed that the present disclosure could realize nucleic acid amplification and detection at the same time, and could effectively reduce an overall detection time of the samples.

Example 10

Figure 16:
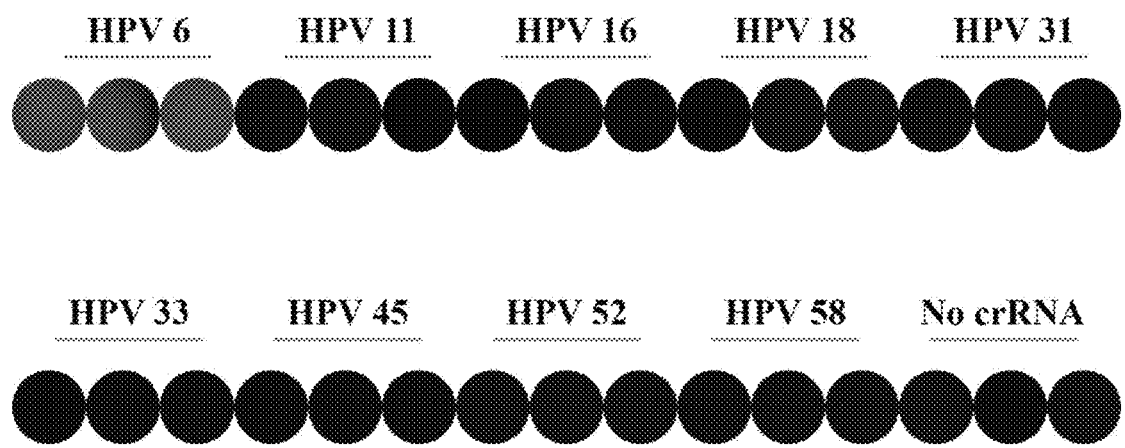
FIG. 16 shows detection results of a clinical sample 1 on the chip.
Figure 17:
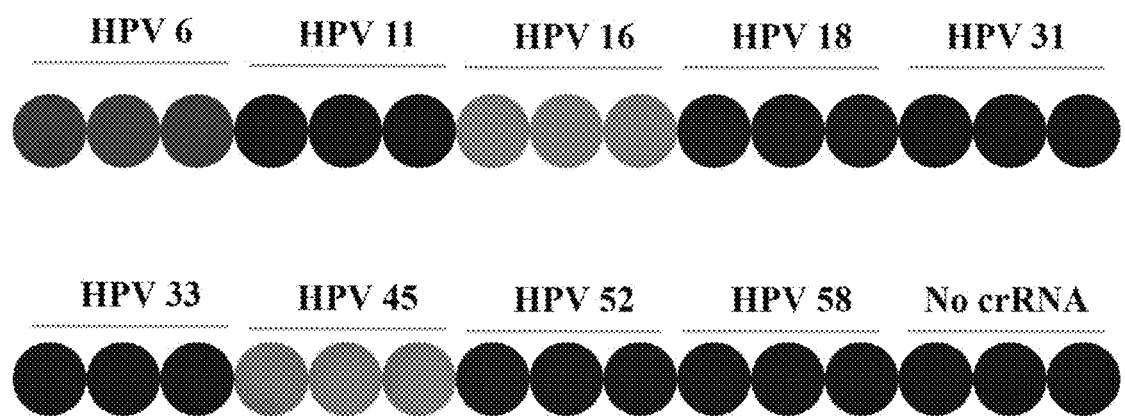
FIG. 17 shows detection results of a clinical sample 2 on the chip.

In this example, it was characterized that the present disclosure could realize the typing of HPV subtypes in clinical samples through a microfluidic chip. Specific operations were as follows:

An amplification solution was prepared according to the instructions in the RPA kit. Primers for the 9 subtypes of HPV 6, HPV 11, HPV 16, HPV 18, HPV31, HPV 33, HPV 45, HPV 52, and HPV 58 were the 9 pairs of primers determined previously (mixed at the same concentration such that a total primer concentration in the amplification solution was 1 μM); while a sample to be tested was 5 μL of clinically collected cervical scrapings that were thermally lysed and added to the amplification system. The amplification was conducted by heating at 39° C. for 20 min. The Cas12a (5 μL, 2 μM) and crRNA of 9 HPV subtypes (10 μL, 1 μM) and 5 μL buffer were incubated at 37° C. for 10 min; and TBA11-FQ (1 μL, 40 μM) was added into 9 obtained mixed solutions. After mixing, 4 μL of a resulting reaction solution was added to the outlet wells 1 to 27 in sequence (for example, the HPV 6 subtype solution was added to the outlet wells 1 to 3, and the HPV 16 subtype solution was added to the outlet wells 4 to 6). 4 μL of a solution that did not contain any Cas12a/crRNA but contained an equal concentration of TBA11-FQ reporter molecule was added into the outlet wells 28 to 30 as a negative control. The sample solution after RPA amplification was injected into the chip from the central sample injection well, and then the chip was placed in a 37° C. metal bath and incubated for 15 min; a green fluorescence photo of each well was taken under a microscope to allow fluorescence analysis. Two clinical samples were initially tested on the chip. FIG. 16 showed the results of the first sample, showing that the fluorescence values in outlet wells 1 to 3 were much higher than those of other outlet wells. This showed that the sample contained the HPV 16 subtype, but not the other eight subtypes. FIG. 17 showed the results of the second sample, it was found that the signals in outlet wells 1 to 3, 7 to 9, and 19 to 21 were significantly higher than the signals in other outlet wells. This showed that the second sample contained HPV 6, HPV 16, and HPV 45 subtypes. The HPV typing results of the two samples on the chip were compared with the clinical PCR detection results. The two results were completely consistent, indicating that the technical solution of the present disclosure had a high accuracy.

What is claimed is:

1. A kit for detecting and typing a plurality of human papillomavirus (HPV) subtypes, comprising a recombinase polymerase amplification (RPA) primer set for the plurality of HPV subtypes, a Cas12a protein, a crRNA set for detecting the plurality of HPV subtypes, and a reporter molecule, wherein RPA primers in the RPA primer set consist of the nucleotide sequences SEQ ID NO: 1 to SEQ ID NO: 18, and crRNAs in the crRNA set consist of the nucleotide sequences SEQ ID NO: 19 to SEQ ID NO: 27.

2. The kit according to claim 1, further comprising a multi-channel microfluidic chip, wherein the multi-channel microfluidic chip has a sample injection well at a center, the sample injection well is connected to one end of each of multiple microchannels, and the other end of each of the multiple microchannels is connected to an outlet well.

3. The kit according to claim 1, wherein the reporter molecule is a biochemical molecule capable of promoting a signal change in a reaction system before and after cleavage of the Cas12a protein, and comprises a single-stranded DNA, a DNA hairpin structure, and a DNA G-triplex or a DNA G-quadruplex; and both ends of the reporter molecule are respectively labeled with a fluorophore capable of conducting fluorescence resonance energy transfer (FRET), or are respectively labeled with a fluorophore and a quencher, or are respectively labeled with a group capable of being detected based on a test strip, or are respectively labeled with a group, a molecule, or a micro-nanoparticle capable of conducting an electrochemical reaction or a plasma resonance.

4. The kit according to claim 1, wherein the RPA primer set has a total final concentration of 0.5 μM to 1.5 μM during amplification.

5. The kit according to claim 1, wherein the RPA primer set has a total final concentration of 1 M during amplification.

6. The kit according to claim 1, further comprising an amplification reaction solution and an enzyme digestion buffer.

* * * * *

SEQUENCE LISTING

```
Sequence total quantity: 27
SEQ ID NO: 1            moltype = DNA  length = 32
FEATURE                 Location/Qualifiers
source                  1..32
                        mol_type = other DNA
                        organism = synthetic construct
SEQUENCE: 1
cagccattag gtgtgggtgt aagtggacat cc                              32

SEQ ID NO: 2            moltype = DNA  length = 32
FEATURE                 Location/Qualifiers
source                  1..32
                        mol_type = other DNA
                        organism = synthetic construct
SEQUENCE: 2
ctggtaataa gttctaaggg cgggcagtca cc                              32

SEQ ID NO: 3            moltype = DNA  length = 33
FEATURE                 Location/Qualifiers
source                  1..33
                        mol_type = other DNA
                        organism = synthetic construct
SEQUENCE: 3
cctttaggcg ttggtgttag tgggcatcca ttg                             33

SEQ ID NO: 4            moltype = DNA  length = 30
FEATURE                 Location/Qualifiers
source                  1..30
                        mol_type = other DNA
                        organism = synthetic construct
SEQUENCE: 4
```

```
catccgattt attggtttgt aagtctgcaa                              30

SEQ ID NO: 5           moltype = DNA   length = 30
FEATURE                Location/Qualifiers
source                 1..30
                       mol_type = other DNA
                       organism = synthetic construct
SEQUENCE: 5
ctgtcccagt atctaaggtt gtaagcacgg                              30

SEQ ID NO: 6           moltype = DNA   length = 30
FEATURE                Location/Qualifiers
source                 1..30
                       mol_type = other DNA
                       organism = synthetic construct
SEQUENCE: 6
ctaatggctg accacgacct acctcaacac                              30

SEQ ID NO: 7           moltype = DNA   length = 30
FEATURE                Location/Qualifiers
source                 1..30
                       mol_type = other DNA
                       organism = synthetic construct
SEQUENCE: 7
cactgggcta aaggcactgc ttgtaaatcg                              30

SEQ ID NO: 8           moltype = DNA   length = 30
FEATURE                Location/Qualifiers
source                 1..30
                       mol_type = other DNA
                       organism = synthetic construct
SEQUENCE: 8
caactgggag tcagaggtaa caatagagcc                              30

SEQ ID NO: 9           moltype = DNA   length = 30
FEATURE                Location/Qualifiers
source                 1..30
                       mol_type = other DNA
                       organism = synthetic construct
SEQUENCE: 9
ctgtcccagt gtctaaagtt gtaagcacgg                              30

SEQ ID NO: 10          moltype = DNA   length = 30
FEATURE                Location/Qualifiers
source                 1..30
                       mol_type = other DNA
                       organism = synthetic construct
SEQUENCE: 10
cactaatacc tacacctaat ggctgcccgc                              30

SEQ ID NO: 11          moltype = DNA   length = 30
FEATURE                Location/Qualifiers
source                 1..30
                       mol_type = other DNA
                       organism = synthetic construct
SEQUENCE: 11
cttgaaatag gtagagggca gccattaggc                              30

SEQ ID NO: 12          moltype = DNA   length = 34
FEATURE                Location/Qualifiers
source                 1..34
                       mol_type = other DNA
                       organism = synthetic construct
SEQUENCE: 12
cctcaataat agtatttata agttctaaag gtgg                         34

SEQ ID NO: 13          moltype = DNA   length = 30
FEATURE                Location/Qualifiers
source                 1..30
                       mol_type = other DNA
                       organism = synthetic construct
SEQUENCE: 13
cccttctccc agtggctcta ttattacttc                              30

SEQ ID NO: 14          moltype = DNA   length = 30
FEATURE                Location/Qualifiers
source                 1..30
                       mol_type = other DNA
                       organism = synthetic construct
```

-continued

```
SEQUENCE: 14
ccaaacttgt agtaggtggt ggagggacac                                   30

SEQ ID NO: 15           moltype = DNA   length = 30
FEATURE                 Location/Qualifiers
source                  1..30
                        mol_type = other DNA
                        organism = synthetic construct
SEQUENCE: 15
cctgtctcta aggttgtaag cactgatgag                                   30

SEQ ID NO: 16           moltype = DNA   length = 30
FEATURE                 Location/Qualifiers
source                  1..30
                        mol_type = other DNA
                        organism = synthetic construct
SEQUENCE: 16
cccactaata cccacaccta aaggctgtcc                                   30

SEQ ID NO: 17           moltype = DNA   length = 30
FEATURE                 Location/Qualifiers
source                  1..30
                        mol_type = other DNA
                        organism = synthetic construct
SEQUENCE: 17
ctcctgtgcc tgtgtctaag gttgtaagca                                   30

SEQ ID NO: 18           moltype = DNA   length = 30
FEATURE                 Location/Qualifiers
source                  1..30
                        mol_type = other DNA
                        organism = synthetic construct
SEQUENCE: 18
ccaatggctg tcctctacct atttcaaggc                                   30

SEQ ID NO: 19           moltype = RNA   length = 47
FEATURE                 Location/Qualifiers
source                  1..47
                        mol_type = other RNA
                        organism = synthetic construct
SEQUENCE: 19
crrnataatt tctactaagt gtagatcctt taccccaatg ctcgccc                47

SEQ ID NO: 20           moltype = RNA   length = 46
FEATURE                 Location/Qualifiers
source                  1..46
                        mol_type = other RNA
                        organism = synthetic construct
SEQUENCE: 20
crrnataatt tctactaagt gtagatatag ggccggtact gtgggg                 46

SEQ ID NO: 21           moltype = RNA   length = 46
FEATURE                 Location/Qualifiers
source                  1..46
                        mol_type = other RNA
                        organism = synthetic construct
SEQUENCE: 21
crrnataatt tctactaagt gtagatctac acctagtggt tctatg                 46

SEQ ID NO: 22           moltype = RNA   length = 46
FEATURE                 Location/Qualifiers
source                  1..46
                        mol_type = other RNA
                        organism = synthetic construct
SEQUENCE: 22
crrnataatt tctactaagt gtagatgaat agagcaggta ctatgg                 46

SEQ ID NO: 23           moltype = RNA   length = 46
FEATURE                 Location/Qualifiers
source                  1..46
                        mol_type = other RNA
                        organism = synthetic construct
SEQUENCE: 23
crrnataatt tctactaagt gtagatatag atcaggcgcg gttggt                 46

SEQ ID NO: 24           moltype = RNA   length = 46
FEATURE                 Location/Qualifiers
source                  1..46
                        mol_type = other RNA
```

```
                    organism = synthetic construct
SEQUENCE: 24
crrnataatt tctactaagt gtagatccac tcccagtgga tcaatg                46

SEQ ID NO: 25        moltype = RNA   length = 46
FEATURE              Location/Qualifiers
source               1..46
                     mol_type = other RNA
                     organism = synthetic construct
SEQUENCE: 25
crrnataatt tctactaagt gtagatttgg cataatcagt tgtttg                46

SEQ ID NO: 26        moltype = RNA   length = 47
FEATURE              Location/Qualifiers
source               1..47
                     mol_type = other RNA
                     organism = synthetic construct
SEQUENCE: 26
crrnataatt tctactaagt gtagatttag ggtccggcaa tttaatt               47

SEQ ID NO: 27        moltype = RNA   length = 45
FEATURE              Location/Qualifiers
source               1..45
                     mol_type = other RNA
                     organism = synthetic construct
SEQUENCE: 27
crrnataatt tctactaagt gtagatcaac tcctagtggc tctat                 45
```